United States Patent [19]

Levina et al.

[11] 3,930,398
[45] Jan. 6, 1976

[54] DEVICE FOR CONTINUOUS TEMPERATURE MEASUREMENT OF DEW POINT OF FLUE GASES

[76] Inventors: Tatyana Abramovna Levina, ul. Snaiperskaya 10, korpus I, kv. 69; Mikhail Borisovich Serkh, ul. Moskvina 5, kv. 46, both of Moscow; Ivan Georgievich Guzynin, Oktyabrsky prospekt 403, korpus 8, kv. 63, Ljubertsy Moskovskaya oblast, all of U.S.S.R.

[22] Filed: July 17, 1972

[21] Appl. No.: 272,624

[52] U.S. Cl. ............................................. 73/17 A
[51] Int. Cl.² ...................... G01N 25/02; G01N 25/68
[58] Field of Search ........................................ 73/17

[56] References Cited
UNITED STATES PATENTS

| | | |
|---|---|---|
| 2,720,107 | 10/1955 | McBriar .................................. 73/17 |
| 3,050,982 | 8/1962 | Vollmer et al. ........................... 73/17 |
| 3,319,457 | 5/1967 | Leone ..................................... 73/17 |
| 3,552,186 | 1/1971 | Sprool .................................... 73/17 |
| 3,623,356 | 11/1971 | Bisberg ................................... 73/17 |

*Primary Examiner*—Herbert Goldstein
*Attorney, Agent, or Firm*—Haseltine, Lake & Waters

[57] ABSTRACT

A device for continuous temperature measurement of the dew point of flue gases, in which the signal of the sensitive unit, carrying information on the appearance of a condensate film on the condensation surface of the dew point temperature transmitter, is applied simultaneously to the regulator of the heating element and the regulator of the cooling element. Both of these are included in the condensation surface temperature control unit, wherein temperature control of the condensation surface is attained by the heating and cooling means operating simultaneously. The transmitter is provided with heating and cooling means.

1 Claim, 3 Drawing Figures

DEVICE FOR CONTINUOUS TEMPERATURE MEASUREMENT OF DEW POINT OF FLUE GASES

The present invention relates to measuring instruments and more particularly it relates to the devices for continuous temperature measurement of the new point of flue gases used, in the main, at heating and power plants and other heat and power installations running on high-sulphur fuels.

Known in the art is a device for continuous temperature control of the dew point of flue gases wherein the signal of the sensitive unit carrying information on the appearance of a condensate film produced by the flue gas on the condensation surface of the dew point temperature transmitter, said transmitter being provided with heating and cooling means, is received by the regulator of the heating element of the condensation surface temperature control unit.

The provision of the heating element regulator in said device makes it possible to carry out continuous measurements of the dew point temperature with a sufficient accuracy within but a narrow range, when the dew point temperature of the flue gas approaches closely the temperature of the transmitter condensation surface at a definite preset flow rate of coolant.

When the dew point temperature is lower than the temperature of the transmitter condensation surface governed by the preset flow rate of coolant, the use of said device for measurements becomes impossible. This prevents the employment of said device at industrial installations in which the temperature of the dew point of flue gasses varies within broad limits which is the case, for example, with high-capacity heating and power plants running on high-sulphur fuel oils.

When the temperature of gas dew point is considerably higher than the preset temperature of the condensation surface, the measurements are practically possible but are characterized by heavy errors which grow still more with an increase in the temperature of the dew point.

An object of the present invention consists in providing a device for continuous control of the temperature of the dew point of flue gases which would be more accurate and capable of being used in a wider range of applications.

This object is achieved by providing a device for continuous temperature control of the dew point of flue gases wherein the signal of the transmitter sensitive unit carrying information about the appearance of the condensate film produced by the flue gas on the condensation surface of the dew point temperature transmitter provided with heating and cooling means is received by the heating element regulator incorporated in the condensation surface temperature control unit wherein, according to the invention, the control unit incorporates a cooling means regulator which receives the signal from the sensitive unit simultaneously with the reception of the signal by the heating element regulator, thereby ensuring temperature control of the transmitter condensation surface simultaneously by the heating and cooling means.

The device according to the invention ensures a high accuracy in measuring the dew point temperature and broadens considerably the field of its application.

Now the invention will be described in detail by way of example with reference to the accompanying drawings, in which.

Figure 3:
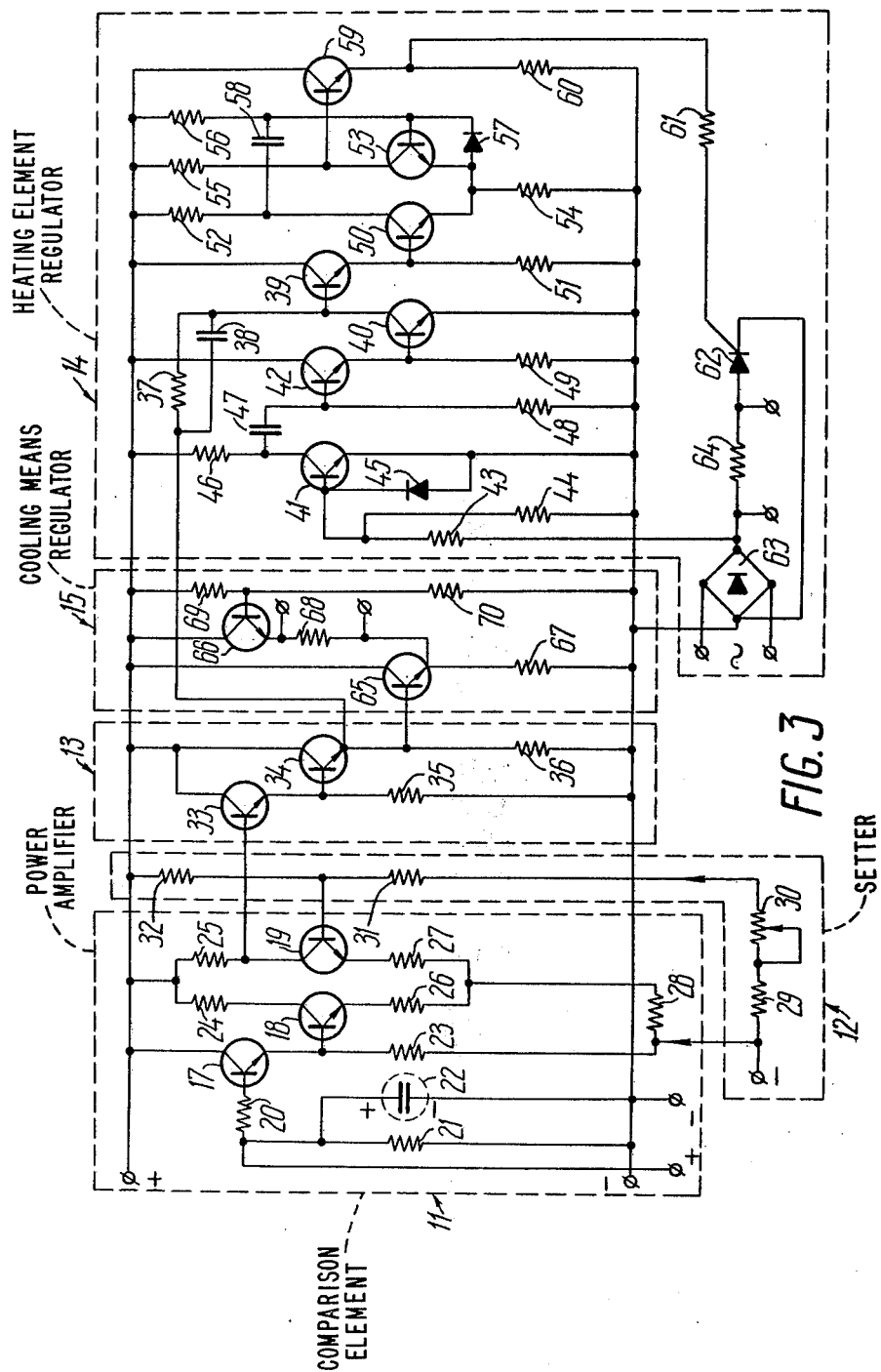

FIG. 3 — same, electrical diagram (without voltage amplifier).

The device for continuous temperature control of the dew point of flue gases according to the invention comprises a transmitter 1 (FIG. 1) of the dew point temperature. The transmitter 1 is a hemisphere made of an electric-insulating heat-resisting material, the external surface of this hemisphere being intended for the condensation of the vapours of flue gases. Located on the condensation surface is a transmitter sensitive unit consisting of two metal electrodes 2 and a thermocouple 3 made integral with one of the electrodes 2.

On the inner surface of the hemisphere, right under the sensitive unit, is located a heating element in the form of an electrical heater coil 4.

The cooling means, i.e., a coolant, is delivered to the condensation surface through a channel 5 provided with a sprayer (not shown in the drawing) and is taken away through a pipe 6.

The lead-out terminals of the electrodes 2, thermocouple 3 and electric heater coil 4 accommodated inside the hemisphere are insulated from the coolant by pipes (not shown in the drawing) made of an electric-insulating material.

This design of the transmitter 1 makes the device suitable for use with any type of coolant (either liquid or gas) required by the conditions of service.

The delivery of coolant can be changed by a control valve 7 actuated by an electric drive 8.

The device is also provided with a unit 9 for controlling the temperature of the transmitter condensation surface, the input of said unit 9 being connected with the electrodes 2 of the sensitive unit of the transmitter 1.

The control unit 9 for regulating the temperature of the condensation surface incorporates a voltage amplifier 10 (FIG. 2) whose lead-out terminal is connected with one of the lead-in terminals of a comparison element 11 whose other lead-in terminal is connected with a setter 12. The lead-out terminal of the comparison element 11 is connected with the lead-in terminal of a power amplifier 13 whose lead-out terminal is connected with the lead-in terminals of the heating element regulator 14 and the cooling means regulator 15.

The lead-out terminals of the heating element regulator 14 and cooling means regulator 15 which serve as the lead-out terminals of the control unit 9 are connected, respectively, with the electrical heater coil 4 and the electric drive 8 of the control valve 7.

The device is also provided with a temperature recorder 16 (FIG. 1) which receives a signal from the thermocouple 3 measuring the temperature of the condensation surface; during operation of the device at a continuous measuring duty this temperature represents the temperature of the dew point of the flue gas being analyzed.

The signal sent by the electrodes 2 located on the condensation surface of the transmitter 1 is amplified by the voltage amplifier 10 (FIG. 2) and fed into the comparison element 11 which comprises three transistors 17, 18 and 19.

Figure 2:
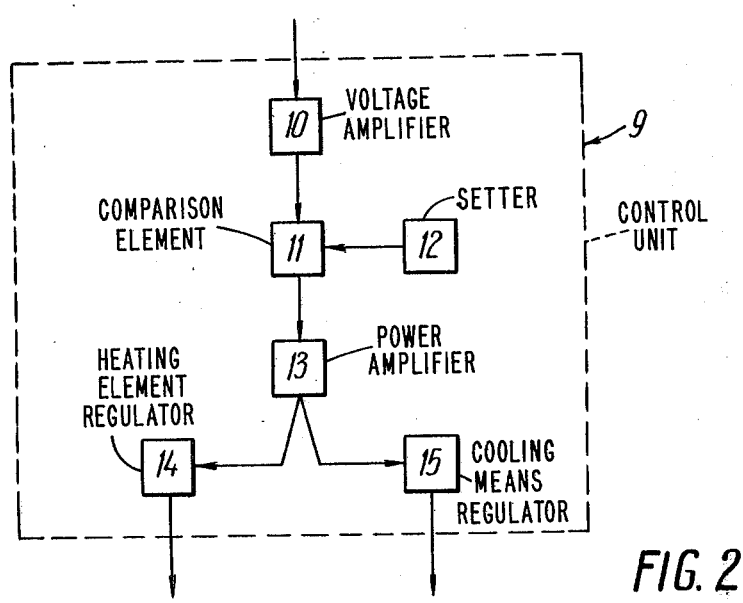
FIG. 2 is a diagram of the temperature control unit of the transmitter condensation surface in the device according to the invention.

The first input of the comparison element 11 (FIG. 3) is the base of the transistor 17 to which a resistor 20 is connected. Also connected to this base is a chain of parallel-connected resistor 21 and capacitor 22, one of the leads of the resistor 21 being connected to the minus terminal of the general power source of the amplifier 10 (FIG. 2). The emitter of the transistor 17 (FIG. 3) is connected with the base of the transistor 18 and with the resistor 23. The collector of the transistor 17 is connected to the plus terminal of the general power source. The transistors 18 and 19 form a balancing stage whose collector load is constituted by the resistors 24 and 25 whose common point is connected to the plus terminal of the general power source while the emitter load is constituted by the resistors 26 and 27 whose common point is connected to the resistor 23 via the resistor 28.

The base of the transistor 19 serves as the second input of the comparison element 11 connected to which is the output of the setter 12. The setter 12 consists of four parallel-connected resistors 29, 30, 31 and 32, the resistor 30 being of a variable-resistance type. The resistor 29 is connected to the minus terminal of a separate power source also connected to the common point of the resistors 28 and 23 while the resistor 32 is connected to the plus terminal of the general power source.

The output of the comparison element 11 is connected with the input of the power amplifier 13 incorporating transistors 33 and 34, the base of the transistor 33 being connected with the collector of the transistor 19. The collectors of the transistors 33 and 34 are connected to the plus terminal of the general power source while their emitters are connected to its minus terminal via resistors 35 and 36, respectively. The emitter of the transistor 33 is connected with the base of the transistor 34.

The output of the power amplifier 13 is constituted by the emitter load; i.e., resistor 36, whose signal is fed to the inputs of the heating element regulator 14 and cooling means regulator 15.

The output of the power amplifier 13 is connected by parallel-connected resistor 37 and capacitor 38 with the input of the heating element regulator 14, this input being at the common point where the base of the transistor 39 is connected with the collector of the transistor 40.

The stages incorporating transistors 39 and 40 constitute a sawtooth voltage generator which is started by a short-pulse former comprising the stages of the transistors 41 and 42.

The base of the transistor 41 is connected across the resistor 43 with the plus terminal of the separate power source having a bridge rectifier circuit and, by a chain of parallel-connected resistor 44 and diode 45, with the minus terminal of the general power source, the diode 45 being connected to the base by its cathode. The collector of the transistor 41 is connected across a resistor 46 to the plus terminal of the general power source while its emitter, to the minus terminal.

The collector of the transistor 41 is connected across the capacitor 47 to the base of the transistor 42; said base is connected, in turn, to the minus terminal of the general power source via the resistor 48. The collector of the transistor 42 is connected with the plus terminal of the general power source while its emitter is connected with the base of the transistor 40 and, across the resistor 49, with the minus terminal of the general power source. The emitter of the transistor 40 is also connected with the minus terminal of the same power source.

The emitter of the transistor 39 is connected with the base of the transistor 50 which, in turn, is connected by the resistor 51 to the minus terminal of the general power source. The collector of the transistor 39 is connected to the plus terminal of the same power source.

The collector of the transistor 50 is connected across the resistor 52 to the plus terminal of the general power source while its emitter is connected with the emitter of the transistor 53 and their common point is connected to the minus terminal of the same power source across the resistor 54. The collector of the transistor 53 is connected across the resistor 55 to the plus terminal of the general power source.

The base of the transistor 53 is connected by the resistor 56 to the plus terminal of the general power source and, by the diode 57, to the common point of the emitters of the transistors 50 and 53, the diode 57 being connected in such a manner that its cathode is turned towards the base.

The base of the transistor 53 is also connected by a capacitor 58 with the collector of the transistor 50. The collector of the transistor 53 is connected with the base of the transistor 59. The collector of the transistor 59 is connected to the plus terminal of the general power source while its emitter is connected to the minus of the same source across the resistor 60.

The emitter of the transistor 59 is connected by the resistor 61 with the control electrode of the thyristor 62 whose cathode is connected to the minus of the separate power source 63 of the bridge rectifier type while its anode is connected to the plus of the same source 63 across the resistor 64.

The output signal of the regulator 14 is taken from the resistor 64.

The output of the power amplifier 13 is also connected with the input of the cooling means regulator 15 incorporating the stages of the transistors 65 and 66. The actual input of the regulator 15 is the base of the transistor 65 whose collector is connected to the plus terminal of the general power source while its emitter is connected with the minus terminal of the same source across the resistor 67.

The emitter of the transistor 65 is also connected across the resistor 68 with the emitter of the transistor 66 whose collector is connected to the plus terminal of the general power source. The base of the transistor 66 is connected to the common point of the voltage divider consisting of resistors 69 and 70 connected, respectively, to the plus and minus of the general power source.

The output signal of the regulator 15 is taken from the resistor 68. The device for continuous temperature control of the dew point of flue gases according to the invention functions as follows.

The dew point temperature transmitter 1 (FIG. 1) is introduced into the flue gas to be analyzed. At the moment of introduction the temperature of the condensation surface of the transmitter 1 is usually lower than the dew point temperature of the gas; as a result, the condensation surface becomes covered with a film of condensate. The electrodes 2 of the sensitive unit generate an electric signal which gives information about the formation of said film.

From the electrodes 2 the signal is fed to the input of the control unit base and, correspondingly, to the input of the amplifier 10 (FIG. 2) which ensures linear amplification of the received signal. The amplified signal is fed to the input of the comparison element 11 whose second input receives a signal from the setter 12, the intensity of said second signal being set when the device is adjusted for the given service conditions. The comparison element 11 utilizes the stages of transistors 17, 18, 19 (FIG. 3) for converting the signals received at its outputs to the values of voltage which are convenient for comparison.

The input signal is fed to the base of the first stage transistor 17 across the resistor 20. The first stage has a circuit with a common collector (emitter follower) which produces a high input resistance of the comparison element 11. The transistor 17 becomes conducting and the signal is fed from the emitter of the transistor 17 to the input of the balancing stage incorporating transistors 18 and 19. The signal is initially fed to the base of the transistor 18, opens the latter and is directed to the emitter of the transistor 19 across the resistors 26 and 27. Simultaneously, the base of the transistor 19 receives a signal from the setter 12 with a separate power source, said signal being set by the resistor 29, variable resistor 30 and resistors 31 and 32.

If the signal at the input of the comparison element 11 becomes more intensive than that on the base of the transistor 19, the transistor 18 will become more conducting than the transistor 19 and the output of the comparison element 11 will produce an unbalance signal. This signal will be fed from the output of the comparison element 11 to the input of the power amplifier 13 based on transistors 33 and 34.

From the collector of the transistor 19 the signal flows to the base of the transistor 33, makes it conducting and the voltage taken off the resistor 35 opens the transistor 34.

The linearly-amplified unbalance signal taken off the output of the power amplifier 13, i.e. from the resistor 36, is fed simultaneously to the inputs of the heating element regulator 14 and the cooling means regulator 15.

The signal fed to the input of the heating element regulator 14 via the chain of the parallel-connected resistor 37 and capacitor 38 is received at the base of the transistor 39 which, jointly with the transistor 40, forms a sawtooth voltage generator. The sawtooth voltage generator is started by the short pulse former based on transistors 41 and 42.

Simultaneously with the signal received at the base of the transistor 39, the base of the transistor 40 receives pulses generated by said former.

The input of the short-pulse former constituted by the base of the transistor 41 receives, across the resistor 43 which limits the input current, the rectified variable voltage from the separate power source 63 of the bridge-rectifier type. In this case the diode 45 inserted between the base and emitter of the transistor 41 limits the back voltage of the "base-emitter" circuit.

The stage incorporating the transistor 41 functions at the switch-over duty. At the moment, when the signal produced by the separate power source 63 is sufficient to open the transistor 41, the latter becomes conducting and, utilizing the differentiating chain of the capacitor 47 and resistor 48, generates short pulses which are fed to the base of the transistor 42 which constitutes an emitter follower. The latter is included into the circuit in order to prevent the input resistance of the transistor 40 from shunting the resistor 48.

The sawtooth voltage is generated on the collector of the transistor 40. At the moment when a pulse is received from the short pulse former, the transistor 40 becomes conducting. The capacitor 38 is charged and opens the transistor 39. The charge of the capacitor 38 also depends on the intensity of the signal received at the base of the transistor 39 from the power rectifier 13. The intensity of this signal governs the voltage to which the capacitor 38 is charged. This changes the amplitude of the sawtooth voltage produced by the sawtooth voltage generator. This shifts the time at which the voltage on the emitter of the transistor 39 reaches the operating level of the single flip-flop oscillator incorporating transistors 50 and 53.

The operating voltage of the single flip-flop oscillator is set by resistors 54 and 55. When the voltage on the base of the transistor 50 reaches the operating level, the transistor 50 opens and the voltage on its collector decreases. The voltage on the plates of the capacitor 58 also decreases which reduces the voltage on the base of the transistor 53 and the latter closes. This increases the voltage on the collector of the transistor 53. When this voltage reaches the level sufficient for opening the transistor 59, the latter becomes conducting and the signal taken off the resistor 60 flows across the resistor 61 to the control electrode of the thyristor 62 which becomes conducting.

At the opening of the transistor 59 the capacitor 58 starts to be discharged through the circuit consisting of the resistor 56, transistor 50 and resistor 54. In this case the transistor 53 is made conducting by the current set by the resistor 56 whereas the transistor 50 closes. Thus, the single flip-flop oscillator generates voltage pulses of certain amplitdue and duration. When the transistor 50 has become non-conducting, the single flip-flop oscillator is ready for the reception of the next sawtooth pulse. The thyristor 62 stays conducting until its supply voltage falls down to zero. At this moment the thyristor 62 will close.

The voltage fed to the input of the short-pulse former from the separate power source 63 whose circuit incorporates the thyristor 62 and resistor 64, synchronizes the pulses received by the control electrode of the thyristor 62 with the current flowing through said thyristor.

Thus, a change in the voltage at the ouput of the power amplifier 13 changes the opening moment of the thyristor 62 and, as a consequence, the effective value of the current flowing through the thyristor 62 and functioning as the output signal of the heating element regulator 14.

Simultaneously with the reception of the signal at the input of the heating element regulator 14, the signal from the ouput of the power amplifiers 13 is received at the input of the cooling means regulator 15. The transistor 65 becomes conducting and the potential on the emitter of the transistor 66 starts growing. In view of the fact that the voltage on the base of the transistor 66 is set by the divider consisting of resistors 69 and 70, said voltage is selected so that the voltage on the base of the transistor 66 would be equal to the voltage on its emitter at a maximum voltage at the output of the power amplifier 13 and, consequently, at the maximum current at the output of the heating element regulator 14. This closes the transistor 66 and cuts off the single at the output of the regulator 15.

At a minimum voltage at the output of the power amplifier 13 and, consequently, at a minimum voltage at the input of the heating element regulator 14 the voltage on the emitter of the transistor 66 becomes lower than that on its base. This opens fully the transistor 66 and produces a maximum signal at the output of the cooling means regulator 15.

Thus, the signals at the outputs of the regulators 14 and 15 are different in intensity and phase.

As a result, the heating element regulator 14 produces a pulse proportional to the thickness of the condensate film formed on the condensation surface of the transmitter 1 (FIG. 1); said pulse is fed for heating the electrical heater coil 4. The current increases with the thickness of the condensate film.

Flowing through the heater coil 4, the current heats the condensation surface of the transmitter 1 until the condensate film is completely evaporated. As the condensate film becomes thinner, the intensity of heating drops and when the film fully evaporates the heating current drops down to zero in correspondence with the zero signal from the electrodes 2.

Figure 1:
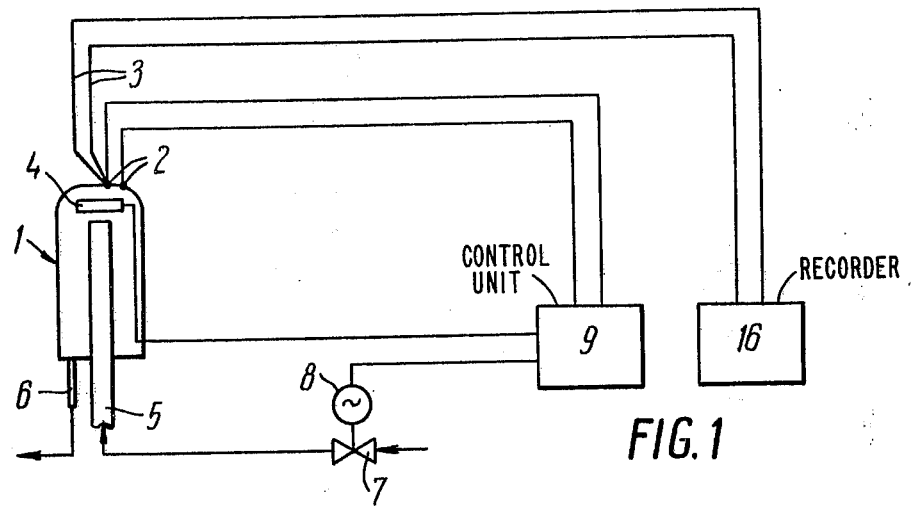
FIG. 1 is a general layout of the device for continuous temperature control of the dew point of flue gases according to the invention.

The cooling means regulator 15 (FIG. 2) generates a pulse inversely proportional to the thickness of the condensate film and controls the flow rate of the coolant by means of the electric drive 8 (FIG. 1).

The flow rate of the coolant decreases with the increase in the thickness of the condensate film which is also conductive to the evaporation of the latter. As the condensate film becomes thinner the flow rate of the coolant increases and, as soon as the film is completely evaporated (the signal sent by the electrodes 2 being equal to zero), the electric drive 8 and the control valve 7 ensure a maximum flow rate of the coolant.

As a result, the condensate film is constantly formed or evaporated on the condensation surface of the transmitter 1 which is characteristic of the surface whose temperature is equal to the temperature of the gas dew point.

Thus, the temperature of the condensation surface continuously measured by the thermocouple 3 and registered by the recorder 16 represents the temperature of the gas dew point.

The design of the control unit 9 (FIG. 2) according to the invention makes it possible to change the temperature of the condensation surface of the transmitter 1 (FIG. 1) by two means simultaneously: a heating element and a cooling means which makes it possible to maintain the temperature of the condensation surface equal to the dew point of the gas with a high accuracy and within a wide range.

The control unit 9 may also be designed so as to control the temperature of the condensation surface by any one of the two above-named means.

For example, when the temperature of the dew point is somewhat lower than the temperature of gas and changes within narrow limits; also in all cases when the temperature of the dew point is higher than the temperature of gas, it is practicable to exercise control by means of the heating element at a constant flow rate of the coolant.

When the temperature of gas is considerably higher than the temperature of its dew point it may become practicable to control the temperature of the condensation surface by the cooling means alone with the heater element inoperative.

In the operating principle of the device described above the proportional control of the condensation surface temperature can be replaced by a more complicated law of control by inserting a separate regulator between the output of the cooling means regulator 15 (FIG. 2) and the electric drive 8 (FIG. 1), said separate regulator ensuring complicated laws of temperature control.

The device according to the invention is characterized by considerable advantages over the known devices for continuous temperature control of the dew point of flue gases.

The use of the cooling means regulator in the device according to the invention and, as a consequence, the possibility of controlling the temperature of the condensation surface simultaneously by the heating and cooling means makes it possible to carry out measurements with a high accuracy and within a wide range.

The device ensures a proportional control of the heating element which provides for a high accuracy in measuring the temperature of the dew point.

The introduction of the regulator with a complex law of cooling means control provides for a further broadening of the range of measurements while retaining their high accuracy.

The use of any type of coolant in the transmitter of the device according to the invention and the location of the heating element directly under the sensitive unit also widens the range of measurements and improves their accuracy.

What is claimed is:

1. A device for continuous temperature measurement of the dew point of flue gases comprising in combination, a dew point temperature transmitter having a condensation surface; means for heating said transmitter, said heating means being located under said condensation surface; means for cooling said transmitter and applied to said condensation surface; s sensitive unit of said transmitter located on said condensation surface thereof; electrodes of said sensitive unit; a thermo-electric element of said sensitive unit; a unit for controlling the temperature of said condensation surface and comprising a heating regulator connected electrically to said electrodes and said heating means, and a cooling regulator connected electrically to said electrodes and said cooling means, a signal from said electrodes carrying information about the formation of a condensate film of flue gas on said condensation surface being applied simultaneously to said heating and cooling regulators, a signal from the output of said heating regulator being directly proportional to the thickness of the condensate film, and a signal from the output of said cooling regulator being inversely proportional to the thickness of said condensate film; and a register electrically connected to said thermo-electric element and adapted to register the condensate surface temperature that is maintained equal to the dew point temperature by said heating and cooling regulators simultaneously.

* * * * *